US011191975B2

(12) United States Patent
Anderson et al.

(10) Patent No.: US 11,191,975 B2
(45) Date of Patent: Dec. 7, 2021

(54) MICRO-COIL WRISTBAND

(71) Applicant: PULSE, LLC, Draper, UT (US)

(72) Inventors: Gregory S. Anderson, Sandy, UT (US); Kade E. Huntsman, Holladay, UT (US); Dale C. Gledhill, Sandy, UT (US); Marc E. Jackson, Draper, UT (US)

(73) Assignee: Pulse, LLC, Draper, UT (US)

( * ) Notice: Subject to any disclaimer, the term of this patent is extended or adjusted under 35 U.S.C. 154(b) by 0 days.

(21) Appl. No.: 15/992,540

(22) Filed: May 30, 2018

(65) Prior Publication Data

US 2018/0272149 A1 Sep. 27, 2018

Related U.S. Application Data

(60) Continuation-in-part of application No. 15/346,208, filed on Nov. 8, 2016, now Pat. No. 10,537,747, and a continuation-in-part of application No. 14/276,172, filed on May 13, 2014, now Pat. No. 10,507,333, which is a continuation-in-part of application No. 13/890,798, filed on May 9, 2013, now abandoned, which is a continuation of application No. 12/502,998, filed on Jul. 14, 2009, now Pat. No. 8,439,816, said application No. 15/346,208 is a
(Continued)

(51) Int. Cl.
*A61N 2/02* (2006.01)
*A61N 2/00* (2006.01)

(52) U.S. Cl.
CPC ............... *A61N 2/02* (2013.01); *A61N 2/004* (2013.01)

(58) Field of Classification Search
CPC ................................. A61N 2/02; A61N 2/004
See application file for complete search history.

(56) References Cited

U.S. PATENT DOCUMENTS

| 4,105,017 A | 8/1978 | Ryaby et al. |
| 4,266,533 A | 5/1981 | Ryaby et al. |

(Continued)

FOREIGN PATENT DOCUMENTS

| WO | WO2012060834 | 5/2012 |
| WO | WO2018085330 | 5/2018 |

OTHER PUBLICATIONS

Advanced Biomagentics® Clinical Database: Osteoporosis Studies, therion®, J. Bone Joint Surg. Am.m http://www.therionresearch.eom/database/osteoporosis.html#2, Mar. 1989;71 (3):411-7.

(Continued)

*Primary Examiner* — Akm Zakaria
(74) *Attorney, Agent, or Firm* — Pate Baird, PLLC

(57) ABSTRACT

An erythrocyte de-aggregation system includes a band, including a strap and housing securing an iron-cored, micro-coil to an appendage, such as a wrist, of a subject to apply a PEMF into a target vessel in the vascular system of the subject. Typically, all of the blood circulates about the body within a matter of a few minutes, some within seconds, thus treating the entire bloodstream over time. The portable PEMF system intensifies both the concentration of electromagnetic flux per unit area, as well as the depth of penetration into the body. The portable PEMF systems relies on the body's circulatory system to eventually pass the body's entire volume of blood past it over a period of time.

20 Claims, 7 Drawing Sheets

Related U.S. Application Data division of application No. 14/276,121, filed on May 13, 2014, now Pat. No. 9,498,639.

(56) References Cited

U.S. PATENT DOCUMENTS

| | | | |
|---|---|---|---|
| 4,315,503 A | 2/1982 | Ryaby et al. | |
| 4,510,704 A | 4/1985 | Johnson | |
| 5,014,699 A | 5/1991 | Pollack et al. | |
| 5,058,582 A | 10/1991 | Thaler | |
| 5,087,336 A | 2/1992 | Liboff et al. | |
| 5,160,591 A | 11/1992 | Liboff et al. | |
| 5,181,902 A | 1/1993 | Erickson et al. | |
| 5,269,745 A | 12/1993 | Liboff et al. | |
| 5,269,747 A | 12/1993 | Erickson et al. | |
| 5,290,409 A | 3/1994 | Liboff et al. | |
| 5,314,400 A | 5/1994 | Tsyb et al. | |
| 5,338,286 A | 8/1994 | Abbott et al. | |
| 5,344,384 A | 9/1994 | Ostrow et al. | |
| 5,370,133 A | 12/1994 | Darby et al. | |
| 5,458,558 A | 10/1995 | Liboff et al. | |
| 5,554,835 A | 9/1996 | Newham | |
| 5,654,694 A | 8/1997 | Newham | |
| 5,743,844 A | 4/1998 | Tepper et al. | |
| 5,792,209 A | 8/1998 | Varner | |
| 5,951,459 A | 9/1999 | Blackwell | |
| 5,997,464 A | 12/1999 | Blackwell | |
| 6,024,691 A | 2/2000 | Tepper et al. | |
| 6,132,362 A | 10/2000 | Tepper et al. | |
| 6,174,276 B1 | 1/2001 | Blackwell | |
| 6,179,772 B1 | 1/2001 | Blackwell | |
| 6,186,941 B1 | 2/2001 | Blackwell | |
| 6,200,259 B1 | 3/2001 | March | |
| 6,213,934 B1 | 4/2001 | Bianco et al. | |
| 6,261,221 B1* | 7/2001 | Tepper | A61N 2/02 600/13 |
| 6,364,824 B1 | 4/2002 | Fitzsimmons | |
| 6,395,799 B1 | 5/2002 | Johnson | |
| 6,418,345 B1 | 7/2002 | Tepper et al. | |
| 6,443,883 B1 | 9/2002 | Ostrow et al. | |
| 6,463,336 B1 | 10/2002 | Mawhinney | |
| 6,560,487 B1 | 5/2003 | McGraw et al. | |
| 6,561,968 B1 | 5/2003 | Dissing et al. | |
| 6,589,194 B1 | 7/2003 | Calderon et al. | |
| 6,675,048 B2 | 1/2004 | McGraw et al. | |
| 6,792,315 B2 | 9/2004 | Carter et al. | |
| 6,819,210 B2 | 11/2004 | Boynton et al. | |
| 6,839,595 B2 | 1/2005 | Tepper et al. | |
| 6,853,863 B2 | 2/2005 | Carter et al. | |
| 6,853,864 B2 | 2/2005 | Litovitz | |
| 6,955,642 B1 | 10/2005 | Simon | |
| 7,010,353 B2 | 3/2006 | Gan et al. | |
| 7,130,692 B2 | 10/2006 | Brighton et al. | |
| 7,158,835 B2 | 1/2007 | Brighton et al. | |
| 7,175,587 B2 | 2/2007 | Gordon et al. | |
| D645,153 S | 9/2011 | Anderson et al. | |
| 8,147,395 B2 | 4/2012 | Anderson et al. | |
| D662,598 S | 6/2012 | Anderson et al. | |
| 8,439,816 B2 | 5/2013 | Anderson et al. | |
| 8,485,960 B2 | 7/2013 | Anderson et al. | |
| 9,498,639 B2 | 11/2016 | Anderson et al. | |
| 2002/0151760 A1 | 10/2002 | Paturu | |
| 2002/0165583 A1 | 11/2002 | Tepper et al. | |
| 2003/0095022 A1 | 5/2003 | Boynton et al. | |
| 2003/0158585 A1 | 8/2003 | Burnett | |
| 2004/0210254 A1 | 10/2004 | Burnett | |
| 2005/0124846 A1 | 6/2005 | Pasula | |
| 2005/0182287 A1 | 8/2005 | Becker | |
| 2005/0249667 A1* | 11/2005 | Tuszynski | A61B 8/08 424/9.3 |
| 2005/0267355 A1 | 12/2005 | Parker | |
| 2006/0212077 A1 | 9/2006 | Pilla et al. | |
| 2007/0293798 A1 | 12/2007 | Hu et al. | |
| 2009/0198293 A1 | 8/2009 | Cauller et al. | |
| 2009/0248098 A1* | 10/2009 | Penny | A61N 2/006 607/3 |
| 2009/0254146 A1 | 10/2009 | Bonmassar et al. | |
| 2010/0280303 A1 | 11/2010 | Dietz | |
| 2013/0072746 A1* | 3/2013 | Burnett | A61N 2/006 600/13 |
| 2013/0244238 A1* | 9/2013 | Neely | B82Y 25/00 435/6.11 |
| 2014/0249354 A1 | 9/2014 | Anderson et al. | |
| 2015/0328476 A1 | 11/2015 | Anderson et al. | |
| 2017/0113060 A1 | 4/2017 | Anderson et al. | |
| 2018/0126185 A1 | 5/2018 | Hochstenbach | |
| 2018/0272149 A1 | 9/2018 | Anderson et al. | |

OTHER PUBLICATIONS

An Electrical Device to Make Bones Grow, http://www.thirdage.com/ebsco/files/14707.html, Medicinal EMFs: Harnessing electric and magnetic fields for healing and health, Science News Online, http://www1.sciencenews.org/sn_arc99/11_13_99/bob2.htm, Nov. 21, 2007.

Data providing the effect of electrical field stimulation on BMD and BMC, http://www.scielo.br/scielo.php?pid=S0100-879X2006005000030&script=sci_arttext, Nov. 21, 2007.

Pulsed Electromagnetic Fields for Bone Health and Bone Healing, QRS World of Health, http://www.qrsworldofhealth.com/osteoporosis_intro.html, Mar. 12, 2008.

Hiromasa Miura, Application of a Pulsed Electromagnetic Field for the Treatment of Osteoporosis, Department of Orthopaedic Surgery, Kyushu University, Nov. 21, 2007.

Kyle Chang , Walter Hong-Shong Chang , Yen-Hsin Yu, Chung Shih, Pulsed Eectromagnetic Field Stimulation of Bone Marrow Cells Derived from Ovariectomized Rats Affects Osteoclast Formation and Local Factor Production, May 14, 2003, (Abstract Only), http://www3.interscience.wiley.com/search/allsearch?mode=viewselected&product=journal&ID=107061128&view_selected.x=69&view_selected.y=9.

Jitendra Behari and Jayanand, Low Level Pulsed Radio Frequency Field and Its Remedial Effect on Osteoporosis and Bone Fracture, Progress In Electromagnetics Research Symposium 2005, Aug. 22-26, 2005, pp. 736-739 Hangzhou, China.

Lirani-Galvááo, C.T. Bergamaschi, O.L. Silva and M. Lazaretti-Castro, Electrical Field Stimulation Improves Bone Mineral Density in Ovariectomized Rats, Brazilian Journal of Medical and Biological Research, Nov. 2006, 1501-1505; http://www.scielo.br/pdf/bjmbr/v39n11/6295.pdf.

Paul Andrew Glazer, Lian Clamen Glazer "Electricity: The History and Science of Bone Growth Stimulation for Spinal Fusion." Orthopaedic Journal at Harvard Medical School, http://www.orthojournalhms.org/ojhms2002/manuscripts/manuscripts-01.htm. Mar. 12, 2009.

Daodaor Technologies Limited, "A New Idea on the Magnetic Products," 258 Zhonghe Zhong Road, Hangzhou, 310003, Phone: 86-571-86559319; 4 pages; Nov. 21, 2007.

American Society of Hematology, Blood Magazine, The Importance of Erythrocyte Aggregation in Blood Rheology: Considerations on the Pathophysiology of Thrombotic Disorders, Haluk Demiroglu, Jun. 1, 1997 vol. 89:4236.

Optimizing Blood Flow, Jonathan Bowen, Oct. 17, 2014.

ElSeveier, Guide for Authors, Rev Bras Hematol Hemoter, 33(4):297-301, Electrical properties of the red blood cell membrane and immunohematological investigation, https://www.ncbi.nlm.nih.gov/pmc/issues/212912/, Mar. 1, 2011.

Wikipedia, Red Blood Cell, https://en.wikipedia.org/wiki/Red_blood_cell, Mar. 28, 2018.

http://www.painandinjurydoctor.com/newsletter/pulsed-electromaanetic-field-therapy-for-joint-pain/, Mar. 28, 2018.

http://www.bloodcytology.com/blood-images/, Mar. 28, 2018.

http://www.rexchimex.com/2018/02/the-relevance-of-rouleaux-formation.html, Mar. 28, 2018.

Sayed, et al., Effect of Pulsed Magnetic Field on Platelets Count and Coagulation Process in Healthy Subjects, Medical Journal of Cairo University, vol. 85, No. 1, 2017 [retrieved on Jul. 22, 2019],

(56) References Cited

OTHER PUBLICATIONS

Retrieved from the internet: <URL: https://pdfs.semanticscholar.org/761f/5d51b796a19fc928593ab09d1303e4be723c.pdf>. pp. 355-361.

* cited by examiner

MICRO-COIL WRISTBAND

RELATED APPLICATIONS

This application a continuation in part of U.S. patent application Ser. No. 15/346,208 entitled IMMERSIVE, FLUX-GUIDED, MICRO-COIL APPARATUS AND METHOD filed on Nov. 8, 2016, which is a divisional application of U.S. patent application Ser. No. 14/276,121 entitled IMMERSIVE, FLUX-GUIDED, MICRO-COIL APPARATUS AND METHOD, filed on May 13, 2014, both of which are hereby incorporated herein by reference in their entireties

BACKGROUND

Field of the Invention

This invention relates to pulsed electromagnetic fields (PEMF) and, more particularly, to novel systems and methods for improving methods for positioning micro coils on a body of a subject.

Background Art

It has long been recognized that chemical reactions and transport processes depend upon the surface area available to participate in the reaction or the transport process. Fick's law of diffusion says that the quantity of mass transported across any distance or barrier is directly proportional to the cross sectional area available to participate. Thus, $m=-kA(C_1-C_2)/(x_1-x_2)$.

This basically states that the amount of mass transported in a diffusion process across a barrier or over a distance is proportional to some constant or proportionality multiplied by a cross sectional area, multiplied by the concentration difference between the starting point and the end point, divided by the distance to be traversed.

Bodily functions on a cellular level typically deal with diffusion through material, such as a liquid in a cell, plasma, or the like. Also, transport processes occur across membranes or cell walls. However, for a cell to participate in a transport process (moving some mass) over some distance along a concentration gradient or through some membrane, a surface area or cross sectional area must be available to participate in that transport process.

Erythrocyte aggregation is a phenonomen that has been observed in cells that are unhealthy, dehydrated, inflamed, affected by an autoimmune condition, or otherwise compromised. Red blood cells (erythrocytes) stack like coins, rather than floating freely in plasma. This greatly limits the surface area available on the cell walls to exchange (transport) nutrients, oxygen, and reaction by products across the cell walls.

It would be an advance in the art to develop a portable system that is unobtrusive to wear, that would permit PEMF therapies to be applied to remediate erythrocyte aggregation in a body. An apparatus, regimen, and method for so doing could greatly advance the availability and effectiveness of PEMF therapies to remediate erythrocyte aggregation.

BRIEF SUMMARY OF THE INVENTION

In view of the foregoing, in accordance with the invention as embodied and broadly described herein, a method and apparatus are disclosed in one embodiment of the present invention as including a system made up of a band containing a housing in which a cavity may receive a cassette containing a therapeutic apparatus. The cassette may include a circuit board and holding various components thereon to effect PENT therapies at a concentrated and localized rate.

The cassette may include a battery and actuators for iron-cored, micro-coils inducing electromagnetic flux directly into and through vascular structures in the human or other body. The band may include a strap or strap portion extending from the housing or housing portion in order to fasten the band and its cassette to an appendage of a user. For example, in one embodiment, the band may strap around a wrist of a user in order to pass PEMF therapies through blood vessels in the wrist.

As a practical matter, a typical human body may contain from about five to about eight pints of blood. Within that blood, the liquid carrier is called plasma. However, various types of blood cells having different functions are present. They have names such as platelets, hematocytes, erythrocytes, thrombocytes, and leucocytes. Red blood cells are called erythrocytes.

Erythrocytes may aggregate causing the reduction of an exposed surface area on the outer walls of those cells. Accordingly, by suitable application of system and methods in accordance with the invention PEMF therapies de-aggregate. Positioning and operating micro-coils, PEMFs are directed intensely through iron-cores in a cassette of the system. Erythrocytes may be de-aggregated, greatly enhancing their effectiveness in exchanging nutrients, waste products, and so forth. Thus, the active blood cells become much more effective in the processes for which they exist.

Pulsed electromagnetic force (PEMF) has conventionally used large coils laid out to be flat, in order that they may be applied to areas of the body. Large voltages are imposed on the coils and the coils cover a comparatively large area, on the order of several square inches (cm) to square feet (decameters), and often approaching a square foot and more. Likewise, such large systems must be stabilized, and are therefore attached to fixed locations. They are applied to wraps, chairs, and the like. Meanwhile, most of the flux (electromagnetic flux or flow), is lost because the direction of the flux path turns too closely about the wires in the coils and is lost.

Meanwhile, whatever amount of the flux proceeds normal (perpendicular) to a particular plane of a large coil is greatly reduced, and thereby largely ineffective. Overall, it has been estimated that about seventy to eighty percent of the magnetic flux applied to a body is lost into space.

Accordingly, a wearable device provides small, powerful, iron-core, micro-coils. The cores provide a unidirectional flux guide for the magnetic flux generated by the micro-coils. Micro-coils may be on the order of fractions of an inch (cm) in diameter, with the cores being typically no larger than from about ⅛ inch to about ¼ inch (⅓ centimeter-½ centimeter) in diameter.

Thus, the magnetic flux generated by the micro-coil and guided by the iron core will be gathered, deeply penetrating, and targeted to a comparatively small area, with a substantial effect. Meanwhile, a system in accordance with the invention relies on the circulatory system of the body to pass all the volume of blood, eventually, past the point at which the wearable device is located.

Due to the high efficiencies, much less power may be used than in conventional PEMF systems, including lower voltages, lower currents, and so forth. Meanwhile, the device may be made so small that it simply covers a small area of the vascular system. For example, a therapeutic device may look much the same as a modern watch and fit on a wrist over suitable arteries or veins.

The device may be provided in colors, and the cassette that contains the battery, electrical circuits and controls, and micro-coils with their cores may be removed as an entire assembly (cassette). This may be done in order to change the color of the band to be a contributing portion of a clothing color scheme, rather than simply black or other neutral and unchanging color.

Since about six to eight pints of blood recirculate in the human body, circulation times are much faster than may be considered. In general, blood volume or weight is considered to be about seven to nine percent of body weight. This blood is recirculated, often as quickly as within twenty seconds. Certain paths that may be remote, and through networks of small capillaries may transport much more slowly, on the order of two to three minutes from the heart to the distant, subdivided capillaries of the vascular structure, and back.

However, blood is pumped out by the heart and circulated by subdividing from larger vessels to smaller, down to capillaries that may each pass cells in "single file." This distribution is followed accumulating from capillaries up through larger veins, until reaching the largest veins for return to the heart. Thus in accordance with the invention, one may rely on a method and apparatus that target significant veins, before they diverge into capillaries, but not necessarily large, core vessels that are deeply buried in the body.

For example, blood vessels along the wrists are sufficiently large for treatment, close enough to the surface for access by PEMF, and of suitable size. A small, wrist-worn PEMF therapy unit may be secured thereto to effectively treat all of the blood in the circulatory system of a wearer.

In certain embodiments, a device may be on for a portion of time, and then off. Currently, it is contemplated that a device will be on (operating, powered) about 25 percent of its time, and off about 75 percent of its time. This will typically provide benefits for health maintenance. With this duty cycle, it has been found practical to manufacture a device that may operate for about two days without needing a recharge.

Alternatively, athletes and others who may be exercising or engaging in physically demanding activities may desire to have a device on full time during the stressful or active time. Thus, such systems may have a duty cycle that never shuts off until affirmatively stopped by a user.

Since erythrocyte aggregation typically stacks up many cells, observed to be on the order of a dozen or more, and typically at least more than eight cells, blood may suffer over 50 percent loss of available surface for mass transport. Meanwhile, inflammation typically causes erythrocyte aggregation. Likewise, in many illnesses, dehydration, and the like may also cause such problems. By applying an apparatus in accordance with the invention, the outer wall or membrane may engage in interaction with electromagnetic waves, in order to negatively charge the outer membrane or wall, thus causing erythrocytes to separate from others.

This PEMF exposure greatly improves the surface area available to participate in transport processes. It renders the bloodstream far more effective in retrieving waste from active cells, and providing nutrition to those cells.

For example, a patient undergoing two years of physical therapy for a damaged shoulder applied PEMF through micro-coils in accordance with the invention for three days in accordance with the appropriate protocols. The result was an ability within those three days to engage in far greater movement than was achieved in the previous two years of physical therapy. Similarly, athletes treated with PEMF by micro-coils in accordance with the invention found the pain and limitations of sprains in the body relieved within two weeks, rather than the conventional six weeks of rest and therapy by conventional methods.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
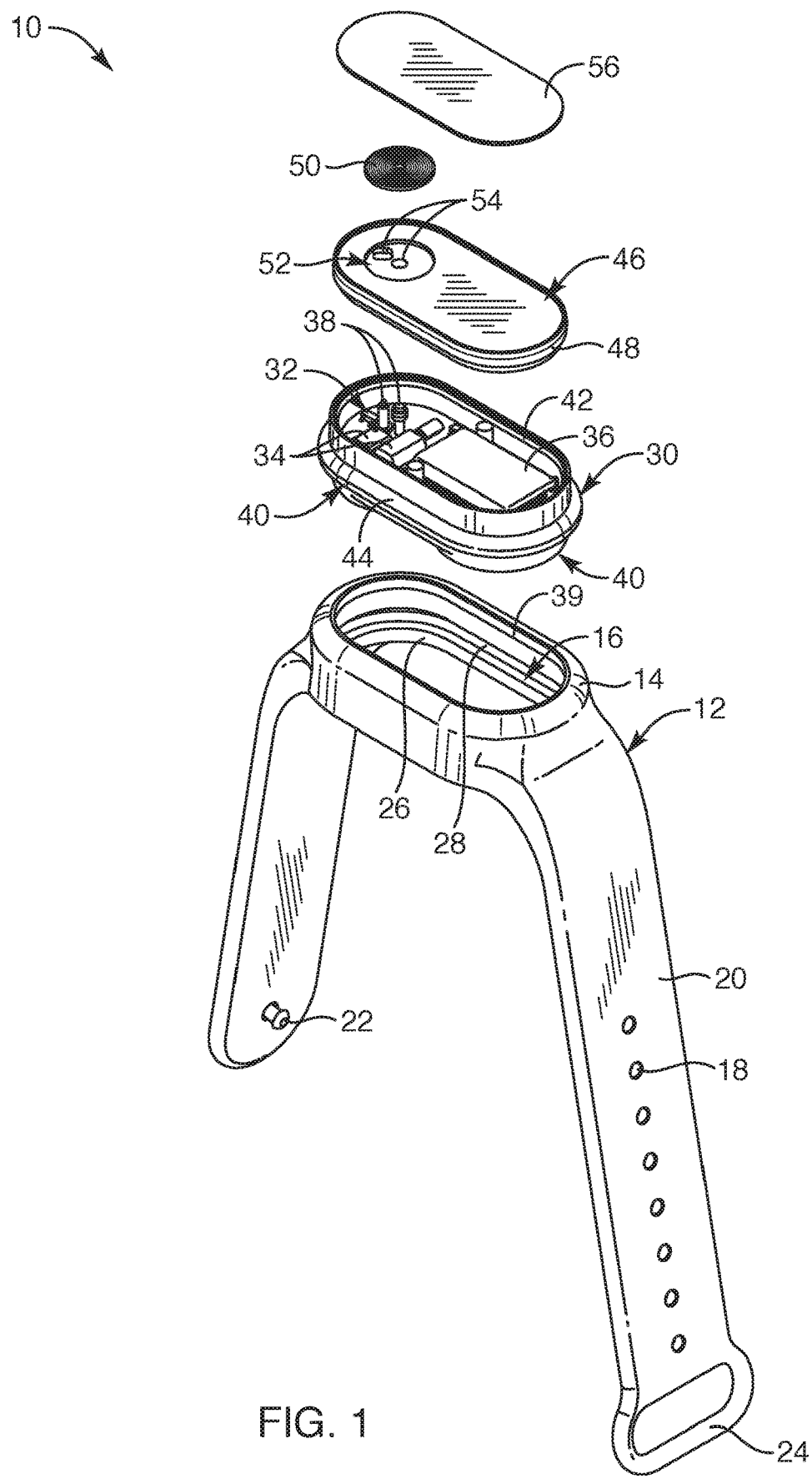
FIG. 1 is an exploded, perspective view of one embodiment of an apparatus in accordance with the invention, including a band holding a cassette with the electromagnetically active components, closed in by a cap, and provided with a cover and a touch sensor or button for operational control by a wearer.
Figure 2:
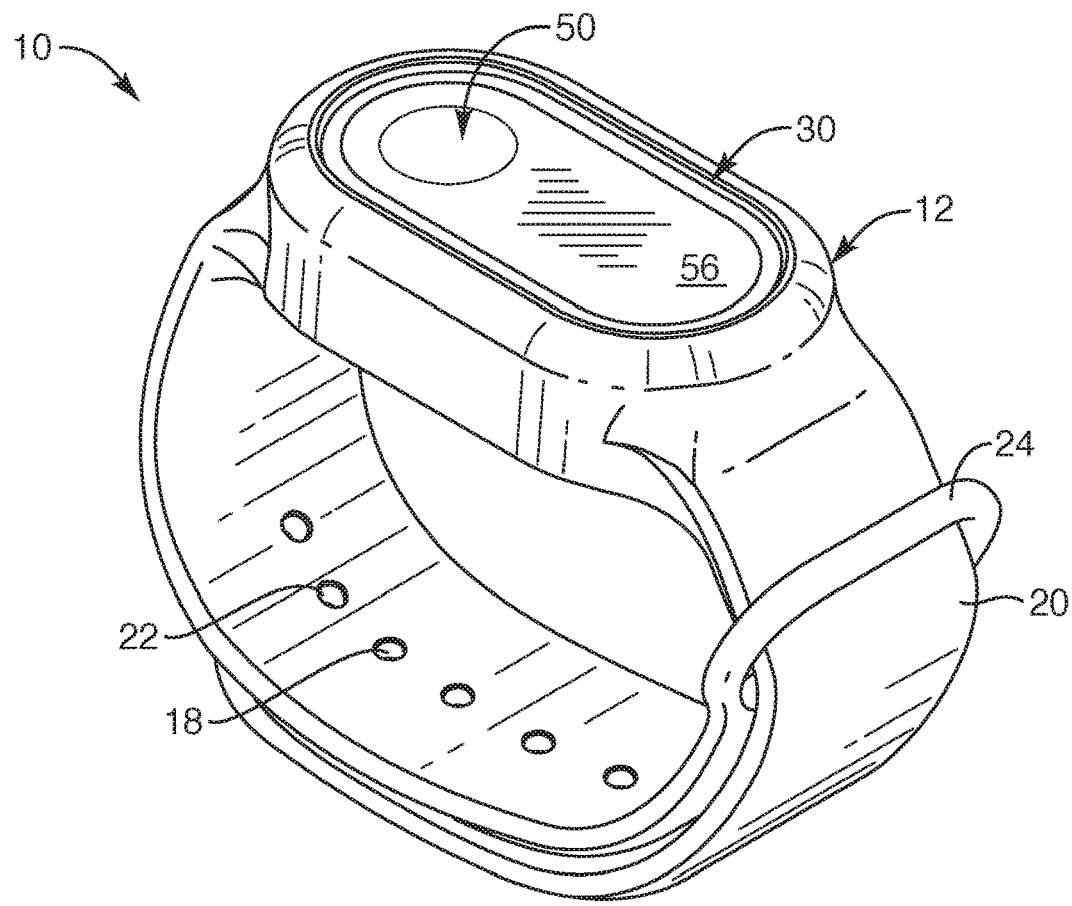
FIG. 2 is a perspective view of an assembled system of FIG. 1.
Figure 3:
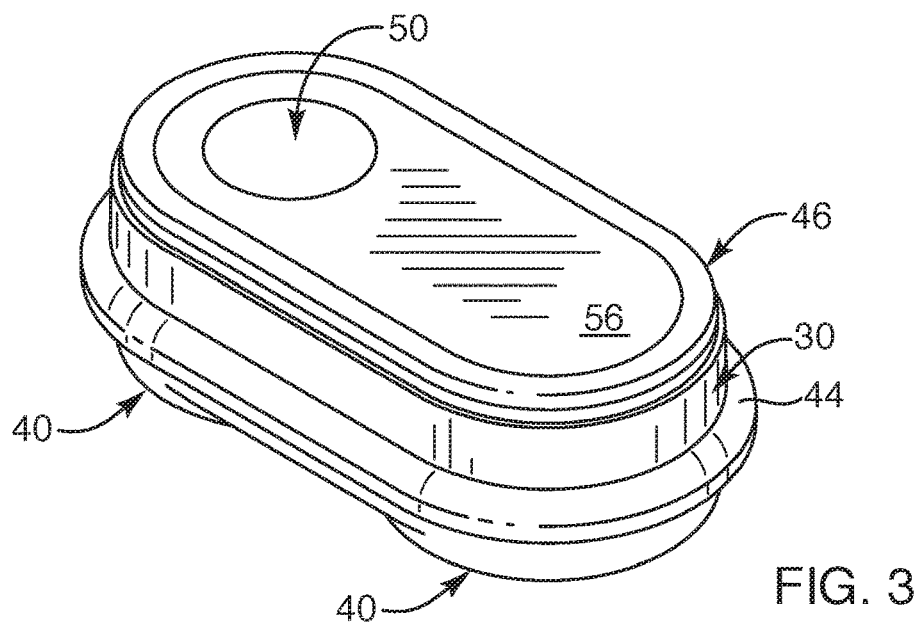
FIG. 3 is a perspective view of the cassette thereof.
Figure 4:
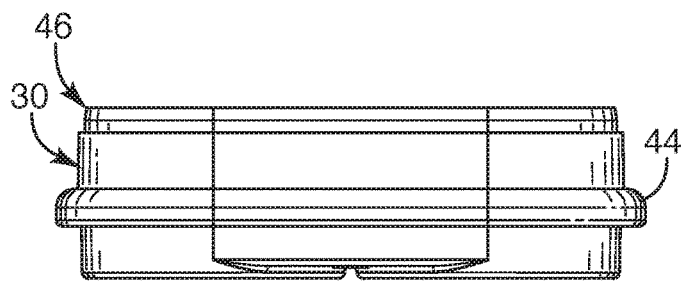
FIG. 4 is a side, elevation view of the cassette.
Figure 5:
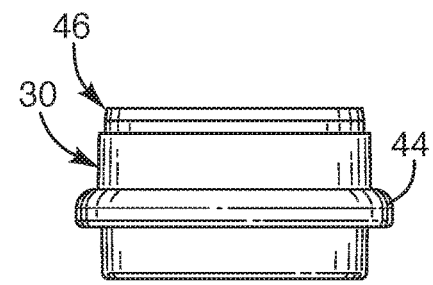
FIG. 5 is an end, elevation view thereof.
Figure 6:
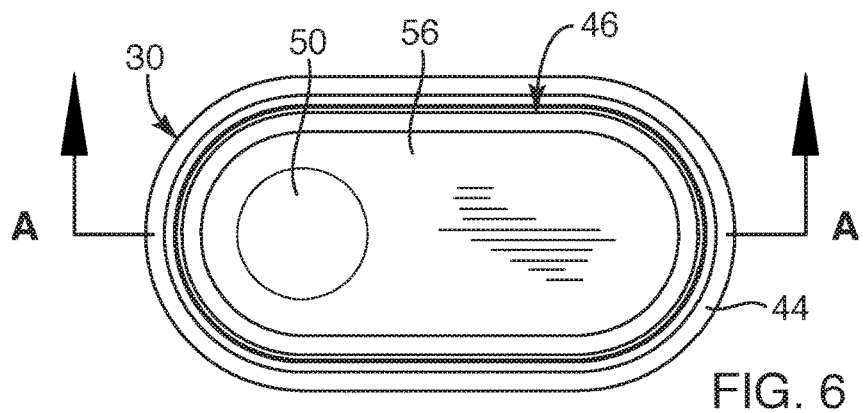
FIG. 6 is a top plan view thereof.
Figure 7:
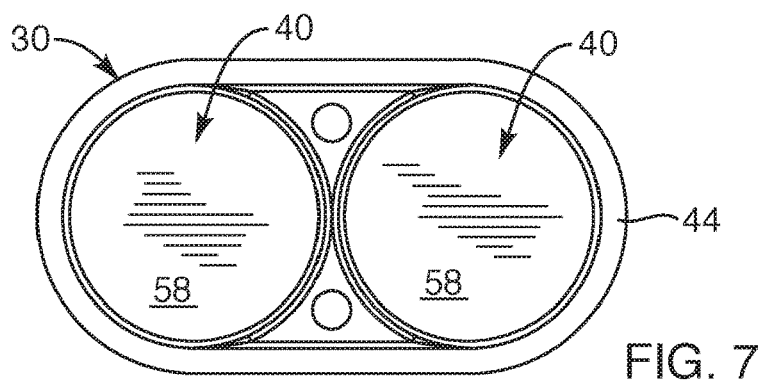
FIG. 7 is a bottom plan view thereof.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of systems and methods in accordance with the invention. The illustrated embodiments will be best understood by reference to the drawings, wherein like parts are designated by like numerals throughout. Referring to FIG. 1, an apparatus in accordance with the invention may be embodied as a system 10 including a band 12 forming a housing 14 defining a cavity 16. Meanwhile, apertures 18 distributed along a strap 20 or strap portion 20 of the band 12 may be configured to rely on a buckle or other mechanism to secure the strap 20 to itself, thus securing the entire band 12 and particularly the housing 14 at a location desired. In the illustrated embodiment, a pin 22 acts to secure one end of the strap 20 to an aperture 18 near another end of the strap 20. A capture 24 may operate much as a belt loop or strap typically associated with a buckle on a belt. In fact, the pin 22 may be replaced by a buckle that relies on the apertures 18 to secure the strap 20 to itself about an appendage (e.g., a wrist, ankle, etc., of a wearer).

Within the housing 14 of the system 10, a ledge 26 may provide a location, for resting or stopping (registering) the insertion of a cassette 30 through the housing 14. Typically, the cassette 30 may snap into a position to rest on the ledge 26, while the lip 28 or ridge 28 acts as a detent 28 to secure the cassette 30 within the cavity 16.

Inside the cassette 30 may be included a circuit board 32 containing various components 34 such as electrical power conditioning, oscillators, timers, on and off buttons or controls, a microprocessor, and the like. The various components 34 may operate to activate or connect a battery 36. For example, actuators 38 or contacts 38 may connect to circuitry controlling the micro-coils 40 to be powered by the battery 36. Typically, the micro-coils 40 may be enclosed within the cassette 30 or enclosure 30 to protect them against moisture, dust, damage, and the like.

In the illustrated embodiment, the detent 42 or lip 42 on the cassette 30 may secure a cap 46 enclosing or otherwise closing the cassette 30. Typically, a ridge 44 or lip 44 on the cassette 30 may snap or deform to snap underneath the detent 28, thus securing the cassette 30 within the cavity 16 of the housing 14 in the band 12.

Similarly, a ridge 48 on the cap 46 may snap into a detent 42 of the cassette 30, in order to secure or seal the cap 46 into the cassette 30. Typically, it will be advisable to make the seal between the ridge 48 of the cap 46 against the detent 42 or lip 42 of the cassette 30 dust proof, and at least somewhat waterproof. This may be done by using elastomeric materials. Elastomeric materials may thus deflect as needed, in order to interact, move, and secure against one another. By proper engineering tolerances, plastics may also server well.

Similarly, although the lip 28 or detent 28 in the housing 14 may hold the cassette 30 by means of the lip 44 or ridge 44 therearound, a seal between the cassette 30 and the edge 49 of the housing 14 is also advisable in order to assure water tight, airtight, dust proof, and so forth sealing. Alternative designs may be developed or constructed that will not require protection against intrusion such materials, and thereby may simplify assembly, manufacturing, tolerances, material choices, and so forth.

The edge 49 may also be thought of as an edge defining the cavity 16. In other words, the edge 49 is a location at which the housing 14 terminates, and the cavity 16 begins at the top or outer surface of the band 12.

A touch pad 50 may be fitted into a recess 52 in the cap 46, in order to be available for operation by a wearer or user. In the illustrated embodiment, the recess 52 is provided with apertures 54 to receive either actuators 38 or contacts 38 that will operably connect the electronic touch pad 50 to the circuit on the circuit board 32. The touch pad 50 is responsible to control programmatically by some series of touches, pressure, and so forth.

In certain embodiments, a cover 56 may be formed of a clear, polymeric material, or glass. Glass has improved maintenance as far as cleaning, although it is more susceptible to damage by impact. Nevertheless, in the illustrated embodiment, a cover 56 may seal against the cap 46, or may be held in a sealing manner by the edge 49 of the housing 14, thereby capturing the cap 46 within the cavity 16. For example, the cover 56 may snap into the cap 46, or both may snap into the cavity 46, to be held by the lip 42 on the outer surface of the housing 14.

Referring to FIGS. 2 through 9, various embodiments of a system 10 in accordance with the invention illustrate the assembled system 10. The entire cassette 30 and its contents are captured within the cavity 16 of the housing 14. Meanwhile, the band 12 to which the housing 14 pertains is wrapped such that the strap 20 at each extremum is wrapped or otherwise held together. The pin 22 in a suitable aperture 18 may hold the strap 20 together to itself or rather its ends to each other. Meanwhile, a simple capture 24 secures the opposite end of the strap 20 against misalignment. Thus one end of the strap 20 holds the pin 22, while the other end contains the capture 24.

Referring to FIGS. 3 through 7, while continuing to refer generally to FIGS. 1 through 13, the cassette 30 may be seen to include structural components and various detents 28, 42, 49 calculated and engineered to have various interference fits in order to assemble the cassette 30 together.

Meanwhile, this embodiment shows two micro-coils 40 captured within the cassette 30. In fact, their locations are illustrated, although the details of the micro-coils 40 cannot be seen, other than their profiles in the floor 58 of the cassette 30 containing them.

The micro-coils 40 may be provided in any suitable number. In the illustrated embodiment, the spacing between the central or center axis of each of the micro-coils 40 may be designed to cover a wrist area. This will render the micro-coils 40 wearable for therapies occurring without requiring a user to be at a specific geographical location, attach larger equipment (e.g., chair, gurney), and so forth.

Figure 8:
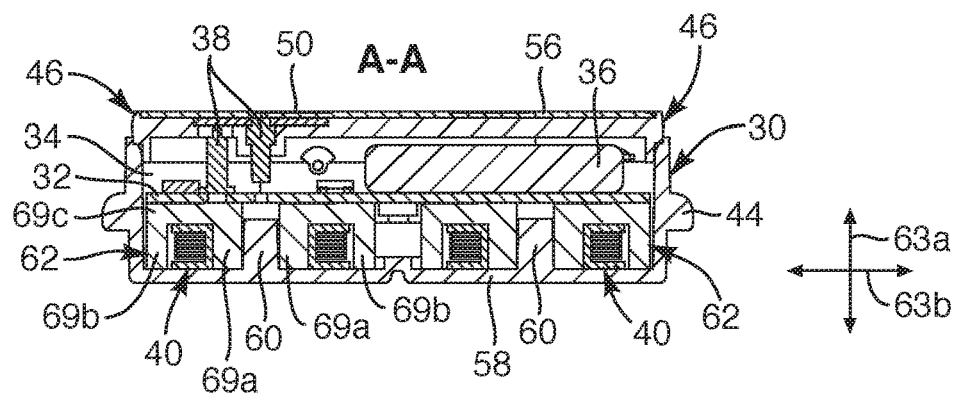
FIG. 8 is a side, elevation, cross-sectional view taken at the line A-A in FIG. 6, this view illustrating the location of micro-coils and their cores, operated by a circuit board and powered by a battery in a system.
Figure 9:
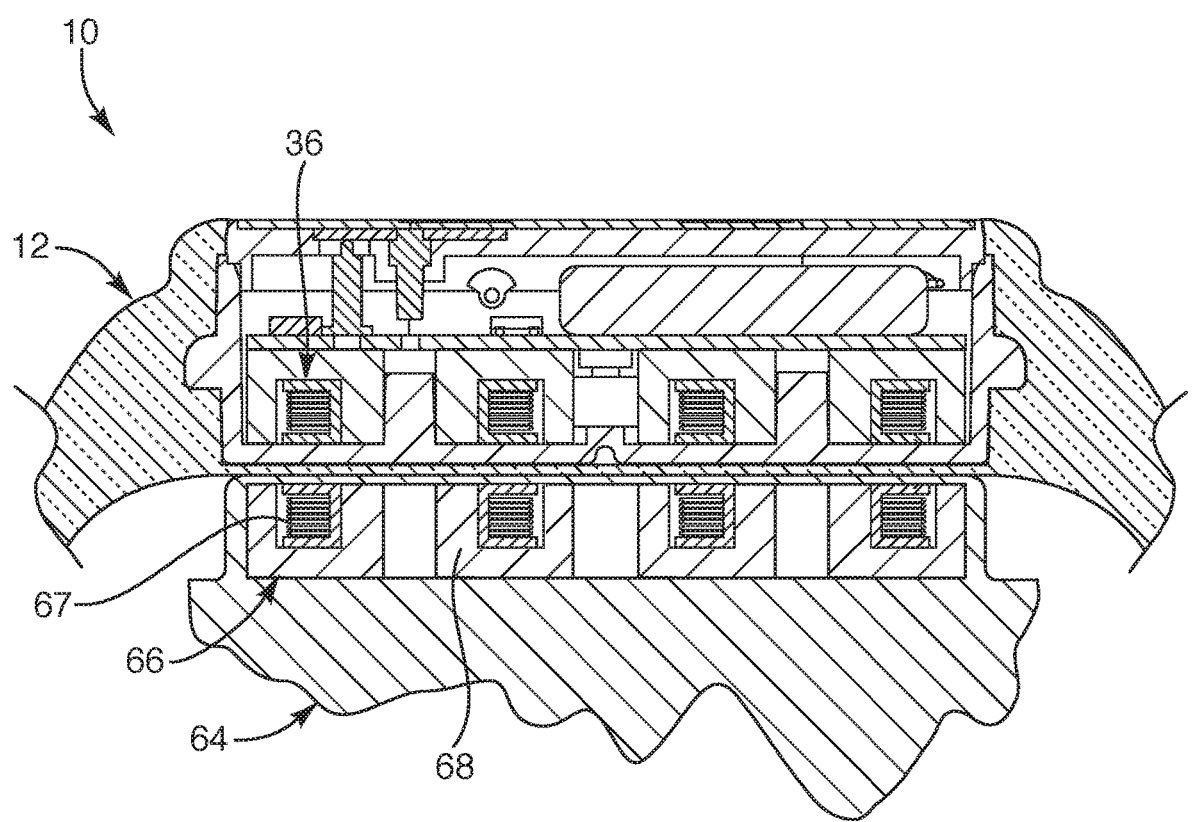
FIG. 9 is a side, elevation, cross-sectional view of one embodiment of a charging station, cut away to extract only the interaction between the charging station and the device or system.

By providing the cored micro-coils 40, the flux density, and therefore the intensity of the PEMF application to the vascular system of a wearer, is intense, directed, and located in close proximity to the blood vessels, and in contact with the skin of a user. Referring to FIGS. 8 and 9 (and FIGS. 1 through 13, generally), the micro-coils 40 may each be formed around a core 62. In the illustrated embodiment, each core 62 may be thought of as being shaped as an 'E' core in a transformer. That is, each of the cores 62 has a central portion 69a, shown as a cylindrical annulus in the illustrated embodiment, as well as outer legs 69b in cross section also, actually configured as a right, circular, cylindrical annulus. Of course the cores 62 connect both legs 69a, 69b solidly along their entire extent. Thus, in some embodiments, the legs 69a, 69b may simply be annuli extending from a back 69c, thus forming a cavity therebetween as the location to receive the coil 40 in an enclosed "track."

A locator 60 or pin 60 may fit as a right circular cylinder between the inner legs 69a, which really amount to an annulus 69a. Meanwhile, the outer legs 69b actually form another outer annulus.

The effect of the core 62, and its specific shape is an effective flux guide 62. That flux guide 62 operates to direct the electromagnetic flux, defined in any physics text as flux lines through an electromagnetic coil, in a much more concentrated, directed, and more deeply penetrating direction, closer together, and therefore at a higher flux density.

This effect is particularly important due to the conventional use of large coils arranged like an old fashioned rag rug. These rugs have been around for centuries, and result from the sewing together of large ropes, where the ropes are themselves formed by braiding together strips of used fabric. These large ropes are then put together, wrapped in a pattern of an oval to cover a large area.

Such a pattern is typical of coils on conventional PEMF equipment. Those coils are typically large, flat loops with open central areas for passing flux. Here, by contrast, the coils are stacked deeply, comparatively, in an axial direction 63a. This reduces the diametric extent of the coils 40 in a radial direction 63b.

The cores 62 are relied upon to both direct flux emanating downward into blood vessels from the coils 40, and to capture the flux lines that must then pass around to the outside of each coil 40, through the outer legs 69b of the core 62. This makes for effective capture of the magnetic flux and maintaining its intensity and directionality down through the inner legs 69a of the core 62, and recapturing it for recirculation about the coil 40 by the path constituted by the outer legs 69b. In reality, to state clearly again, the legs 69a are actually a single cylinder 69a illustrated here. They could be rectangular 'E' legs as in a transformer. Likewise, the outer legs 69b, actually constitute a single annulus 69b of metal.

Referring to FIG. 9, while continuing to refer to FIG. 8, and FIGS. 1 through 13 generally, a recharging process may rely on a base 64 holding a transformer half constituted by coils 67 and cores 68. In the illustrated embodiment, the transformer half 66 may engage the coils 40 and their cores 62 as described hereinabove to form a complete transform. Alternatively, the charging circuit may operate separately from the micro-coils 40 as a transformer for recharging as known in the art.

The circuit board 32 may be equipped with the circuitry, and the microprocessor as a controller. It may switch the operation of the micro-coils 40 and their cores 62 to form a complete transformer passing magnetic flux lines from the center of the core 68 into the inner annulus 69a of the core 62. The flux lines proceeding around the micro-coil 40 and back through the outer legs 69b or outer annulus 69b of the core 62 to pass into the outer portion of the core 68 about the coil 67.

Thus, the micro-coils 40 and their cores 62 may operate as a transformer half 66 juxtaposed against the transformer half 66 with its coils 67 and cores 68. Since the core 68 becomes a magnet under the influence of the coil 67, once energized, the cores 68 become magnets attracting the metal of the cores 62 associated with the micro-coils 40 in the system 10. Alternatively, another magnet may provide this attracting force.

Figure 10:
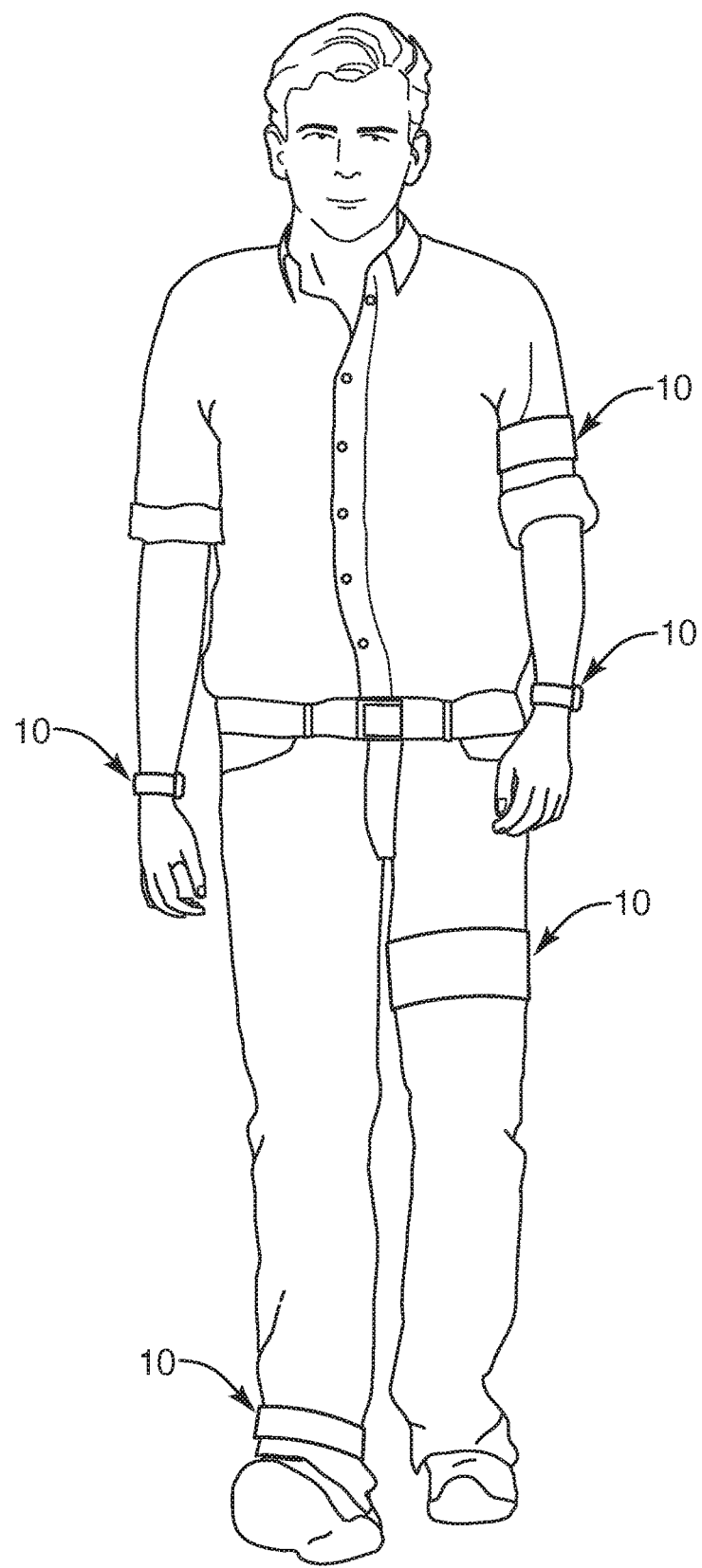
FIG. 10 is a perspective view of a wearer or a user illustrating various locations where a system in accordance with the invention may be secured to a user or clothing, or even embedded within the clothing.

Referring to FIG. 10, by suitable sizing and shaping of the band 12, a band 12 may be attached about an appendage of a user. For example, an ankle bracelet may fit about an ankle of a user in order to secure the activated cassette 30 over blood vessels in an ankle. A wrist of a user may have the cassette 40 placed over the outside surface of a wrist, or the inside (back hand side, and palm side, respectively) of a wrist of a user.

Meanwhile, the cassette 30 may be manufactured in a comparatively flat configuration to be received in pockets of clothing, or in regions of clothing, such as might fit about a thigh of a user, an upper arm, a lower arm, or the like.

One advantage of the wrist-mounted system 10 is that the system 10 may appear the same as a watch, or a health monitoring bracelet very common in exercise today. Likewise, colors, shapes, and the like for the band 12 may be selected to complement other apparel. Some may be configured in colors and shapes that tend to be associated with feminine use, while others may be colored and shaped to correspond to perceived masculine use.

Nevertheless, notwithstanding the proximity to the skin surface that blood vessels have in the wrists, femoral arteries in the legs, and axillary vessels in the upper arm may also be appropriately targeted. In fact, a cap or even a turtleneck shirt may even be fitted to operate near a carotid artery or jugular vein in the neck of a user. Other articles of clothing may be adapted to unobtrusively contain cassettes 30 in accordance with the invention in order to provide a regular, wearable, transportable regimen for PEMF therapy.

Figure 11:
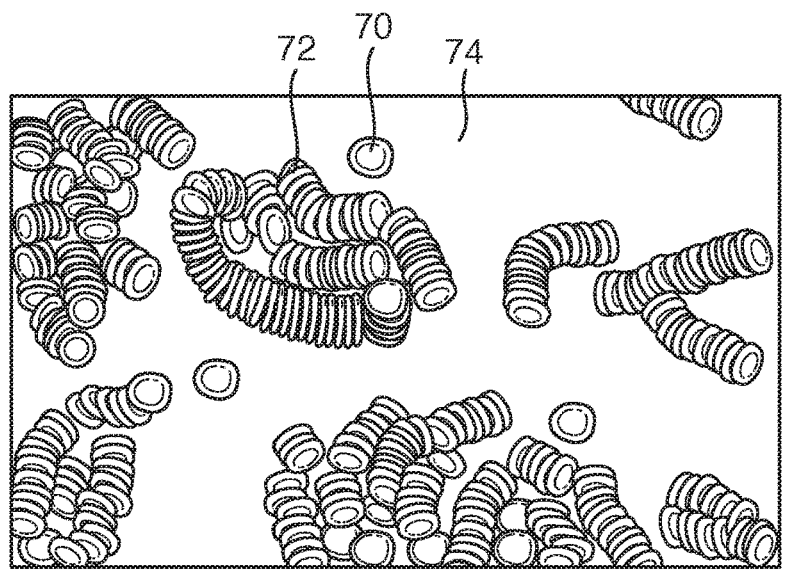
FIGS. 11 and 12 are drawings of example images from micrographs (photographic images taken by a scanning electron microscope), showing aggregated erythrocytes in two different, actual, blood samples.
Figure 12:
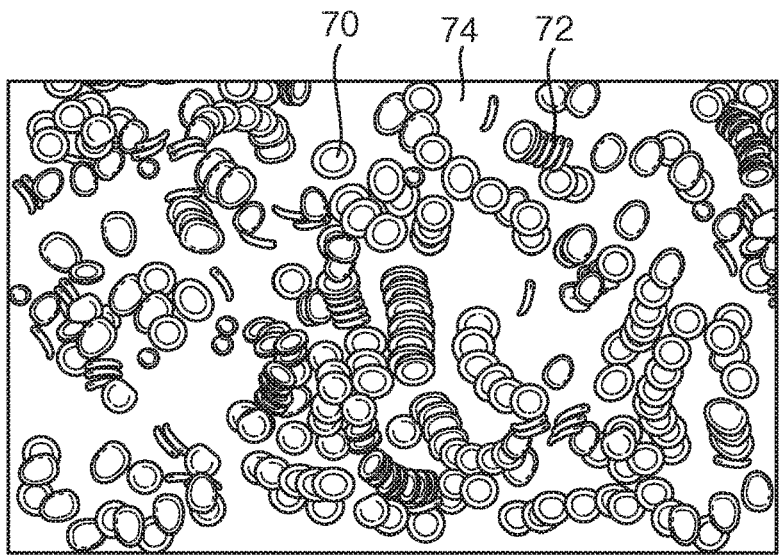
Figure 13:
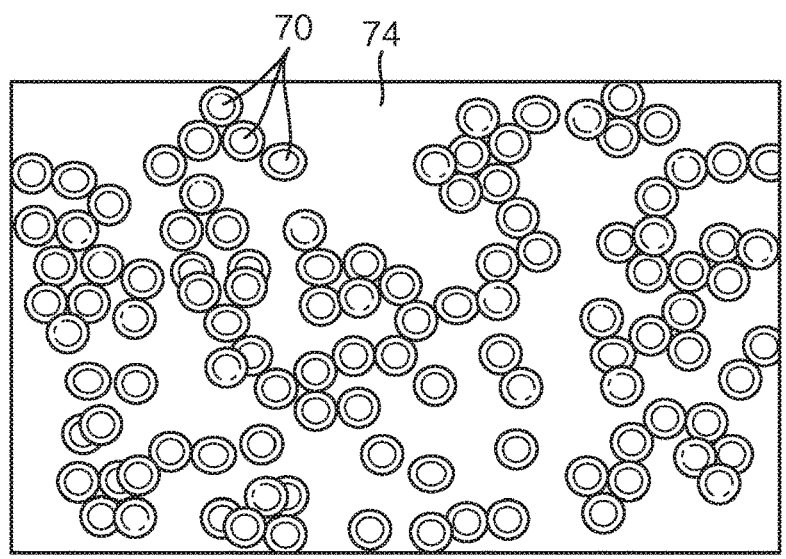
FIG. 13 is a drawing of a micrograph of blood of the same subject as FIG. 12, with this blood sample drawn after applying a regimen of PEW with micro-coils operating in accordance with the invention.

Referring to FIGS. 11-13, actual tests conducted with a system 10 in accordance with the invention have been applied to cells 70 within a liquid carrier 74, plasma 74. FIGS. 11 and 12 are images of tests following a first instance of a blood draw. The drawings are from photographs provided by a scanning electron microscope. Such images are referred to as micrograph. The cells 70 have agglomerated in an aggregation 72 as described hereinabove.

In contrast, FIG. 13 is the results of another instance of the same test. The micrograph was created by imaging blood plasma 74 and blood cells 70 of the subject corresponding to FIG. 12. This result is typical of numerous test images following a recommended dosing. In each instance, a PEMF was applied to blood vessels in a wrist of a wearer (subject) by a system 10 in accordance with the invention.

Aggregations 72 of cells 70 were universally dispersed systemically by a PEMF applied locally to blood vessels in that single wrist. Cells no longer aggregated as in FIGS. 11 and 12. Rather they became mutually repellant and thereby separated, tending toward uniform distribution as illustrated in FIG. 12. Even larger population densities of cells 70 in plasma 74 than those of FIG. 13 distributed uniformly.

Figure 14:
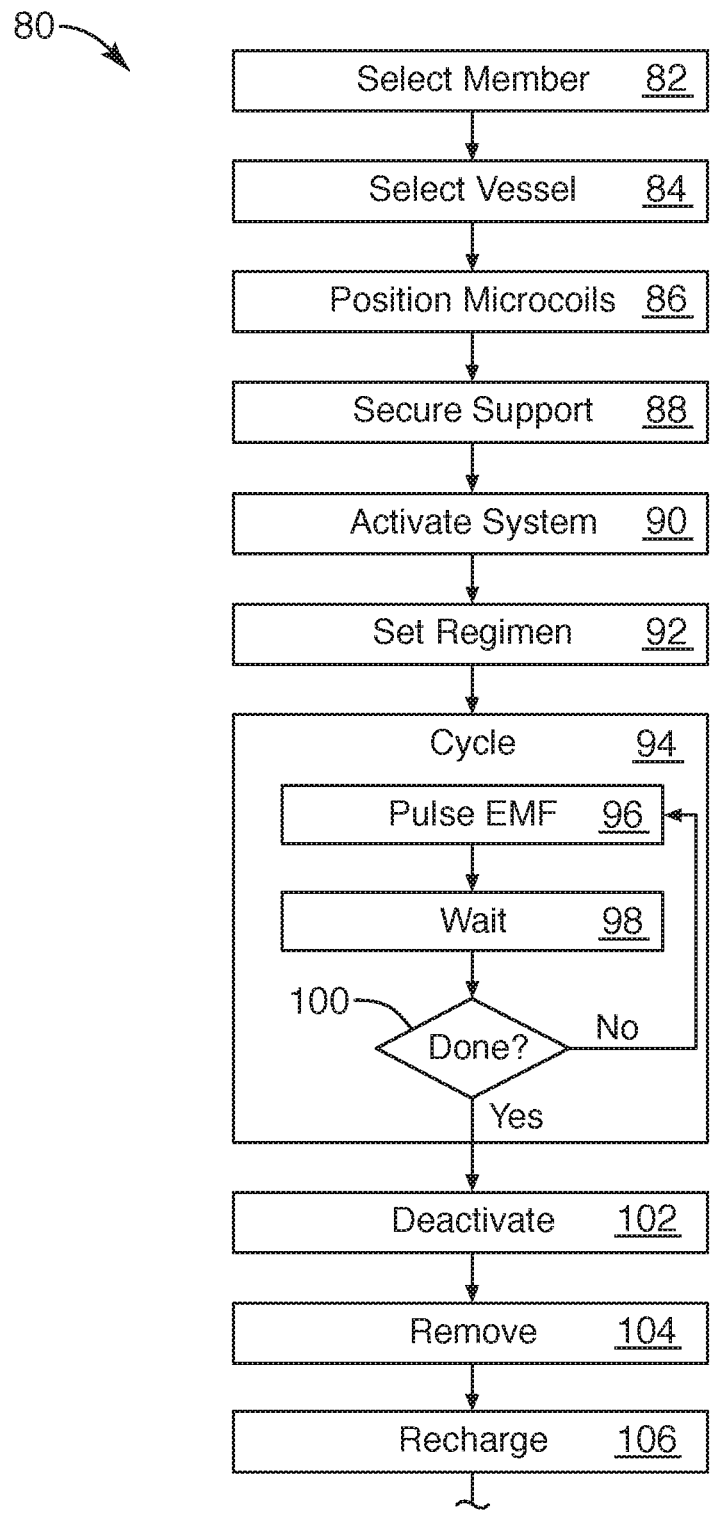
FIG. 14 is a schematic block diagram of a process for using an apparatus in accordance with the invention.

Referring to FIG. 14, while continuing to refer generally to FIGS. 1 through 14, a process 80 of use of an apparatus 10 in accordance with the invention, may involve selecting 82 a bodily member. The member selected may depend on convenience. For example, in a clinical setting, access by a medical professional may be more important than mobility or non-interference with the motion of activity, such as exercise or the like.

For example, an active wearer might prefer a system 10 that occupies no more space, and provides no more interference, than a modern watch or exercise monitoring system. Thus, a wrist location may be preferable. On the other hand, the patient who has been dressed for such activity may be fitted with clothing containing an apparatus 10 on the upper or lower arm, an ankle, thigh, lower leg, neck, head, thorax, or the like. Wherever suitable blood vessels may be accessed by the system 10.

Selecting 84 a vessel may be constituted primarily in accessing 84 a vessel suitable for locating 86 or positioning 86 the micro-coils 40 thereabove (on the skin). Above is not literally vertically above, but radially outward from a blood vessel. For example, in a wrist, the micro-coils 40 may be secured on the back hand side of a wrist of a user. On the other hand, micro-coils 40 may be positioned on the palm side of a wrist of a user, thereby accessing different blood vessels. In fact, the system 10 may access arteries or veins, arteries being the aerated and delivery cells 70, and veins carrying the waste-containing returning cells directed to the heart.

In selecting 84 a vessel (blood vessel) to act as the center of a treatment regimen, considerations may include the nature of the vessel (e.g., whether the vessel is an artery or a vein), the proximity of the vessel to the surface of the skin, or the size of the blood vessel. One may consider the time for recirculating from the heart to the blood vessel and back to the heart, the fraction of circulation, and the like. As a practical matter, selecting 84 a blood vessel may be a decision that is made universally for particular models of a system 10.

For example, certain systems 10 may be designed and manufactured to be used around an ankle, based on the specific blood vessels that will be targeted by the system 10. Similarly, wrist-borne systems 10 may be designed to target vessels on the outside (back hand), side of the wrist, or the inside (palm) side of a wrist. Likewise, upper arms, neck, head, or other locations of arteries or veins, considered candidate vessels, may be selected 84.

Systems 10 may be designed to operate in a way adapted to the particular location. Thus, in general, selecting 84 may be a decision that affects where the system 10 is applied.

Ultimately, in order to begin, a regimen is initiated by positioning 86 the micro-coils 40 at the location selected 84, targeting the appropriate vessels. In one currently contemplated embodiment, a pair of micro-coils 40 in a band 12 may be placed over a wrist, around an ankle, or the like. The wrist is particularly well adapted to use of a system 10 due to the geometry. The wrist has comparatively flat sides or surfaces. The wrists of the two arms of a user are not in close proximity. In comparison, on the leg or ankle, a system 10 may be more subject to impact, may cause interference with walking, or the like.

Thus, upon positioning 86 micro-coils 40, the strap 20 may be closed by securing the pin 22 through the capture 24 to engage in aperture 18. Other embodiments may include a buckle or other fastener of suitably adjustable type to replace the aperture 18 and pin 22 system. Thus, securement 88 of the supporting subsystems 12, 20 may secure the housing 14 with its content, the cassette 30 holding micro-coils 40, in the desired location selected 84.

The system 10 may be activated 90 by an appropriate activation of the touch sensor 50 or button 50 on the cassette 30. Numerous capacitive buttons 50, thermal detection buttons 50, pressure sensitive buttons 50, heat sensing surfaces 50, and the like may operate as the pad 50 or sensor 50 in the cassette 30. Likewise, commands may be given by any suitable mechanism, such as movement of a digit (finger) of a user across the sensor 50, touching, pressing, multiple touches, or the like. Such systems are well understood in the art of electronics, and any may be suitable, including micro switches, capacitive switches, or touch sensitive and motion sensitive sensors, common to smart phones.

Similarly, setting 92 a regimen may also be done by coded signals received through the button 50, as established by a user. In some embodiments, regimens may be cycled through as a matter of choice in a menu, or otherwise activated. Again, various selection systems are well known in the art, and menus may be displayed on a screen constituting a part of the cover 56, or seen on the cap 46 and covered by a clear cover 56. In other words, a screen may be embedded into the cap 46, such that the top surface of the cap 46 represents a screen on which information may be presented. Again, the focus of the instant invention is not the exact electronic mechanisms by which buttons 50 and screens are embedded in the cap 46 and supported by the circuit board 32 in the cassette 30.

Cycling 94 may include pulsing 96 the electromagnetic field for some period of time at its frequency or range of frequencies. Pulsing 96 may be continuous. In other embodiments, a pulsing 96 may be interrupted by a wait 98 or a delay 98 between series of pulsing 96.

For example, it has been found suitable to pulse 96 a system 10 for about twenty five percent of the real passage of time. In one contemplated embodiment that has produced positive results, pulsing 96 has proceeded for about seven minutes. Thereafter, a delay time 98 or wait 98 of 23 minutes, about triple that pulsing 96 time has occurred. Nominally, a ratio of about one to four has been found suitable. Actual experiments relied on pulsing 96 for about seven minutes and delaying 98 for twenty three minutes, slightly over triple the time of the pulsing 96.

In general, cycling 94 may undergo a test 100 periodically to determine whether the process 80 is over. For example, an entire cycling 94 period may repeat the pulsing 96 and waiting 98 repeatedly for an entire day, or until the system 10 is powered off. In other embodiments, programming or setting 92 may establish the cycling 94 itself to continue with pulsing 96 and waiting 98 for some overall period of activity.

In yet other embodiments, pulsing 96 may continue until the test 100 determines that the process 80 is done, either for a timing criterion, or for a power-shut-off criterion. In either event, the test 100 is responsible to move forward the cycling 94 to de-activate 102 the system. If, however, the test 100 determines that operation is not completed, that cycling 94 is not done, then the process 80 returns to pulsing 96 within the cycling 94 of the process 80.

Ultimately, when the cycling 94 is completed, for reason of choice of a user, pre-programmed regimen, pre-timed cycling 94, or the like, de-activation 102 powers down the system 10. The electronic and electrical components 34 may still be powered by the battery 36, but the micro-coils 40 are disconnected from power.

At that point, the system 10 may be removed 104 from a user. Removal 104 may typically include opening up the strap 20 of the band 12 in order to recharge 106 the battery 36. In the illustrated embodiment of FIG. 9, recharging may be done by a transformer process that does not require electrical contact, but rather simply electromagnetic engagement between a recharging transformer half 66, and magnets, electromagnetics, or both in the cassette 30.

Of course, recharging 106 may be done directly by an electrical connection to the battery 36, with appropriate recharging 106 bridges and rectification as needed. However, the cassette 30 may be more robust if completely sealed against water, dust, air, and other materials that may compromise it or otherwise diminish its life, if the cassette 30 can be sealed. Thus, an electrical connection is a source of failure, and a requirement for a penetration into the inner cavity of a cassette 30.

Recharging 106 may occur days later, or in the same day. Typically, in systems 10 in accordance with the invention, tested 100 with actual subjects, recharging with suitable activity is not required more often than about every couple of days. Power requirements depend on duty cycle during the cycling 94. Duty cycle may represent the amount of time of pulsing 96 compared to the total time of pulsing 96 plus waiting 98. Also total pulsing 96 may be considered with respect to total time "on" as a duty cycle or a percentage of time on duty.

Likewise, the time that cycling 94 occurs compared to the time that the system 10 is done 100 and de-activated 102 may also be considered another measure of cycle time. Typically, the proportion of pulsing 96 in which electrical activation of the micro-coils 40 relies on draining power from the battery 36 may be considered the "on" time globally. Then, cycling 94 may be the focus as a duty cycle representing the proportion of time in which pulsing 96 occurs compared to all total time passage. Thus, there are at least three ways to calculate duty cycle.

However, the battery 36 is most affected by the pulsing 96 or other activity draining power from the battery 36, compared to all other time in which the battery 36 is powering sensors, displays, stand by conditions, but not being significantly drained.

In one currently contemplated embodiment, the battery 36 operates at three volts to control the micro-coils 40. The micro-coils 40 wire wrapped around a core eighteen millimeters in outside diameter, and four millimeters thick (length for the coil 40). Typically, 20 to 40 gauge wire is used, with 20 to 200 turns on each coil 40 with 90 turns giving a suitable size and effect. The base thickness (axial length) of the iron core 62 is 0.2 inches to 0.4 inches (½ to 1 centimeter) with a target between 0.2 and 0.25 inches (0.5-0.6 cm). The wall thickness of the cylindrical cores 62 is minimal molding thickness for strength.

The micro-coils 40 in the illustrated embodiment are connected electrically in series, and thus each is running a current of a suitable amperage for the voltage applied. In successful tests of a system 10 in accordance with the invention the current was 0.01 amperes (amps). Thus, the size of the battery 36 will fit into the cassette 30 as illustrated in the proportional size of a watch as illustrated with respect to the band 12.

Duty cycles for tests to determine recommendations resulted in a first mode that pulses 96 for seven minutes followed by a rest 98 or delay 98 of twenty three minutes before repeating the pulsing 96. This regimen is repeated for a timed limit of about twelve hours. Nevertheless, the regimen is not deemed harmful, and therefore may continue for beyond twelve hours. Thus, if a user controls the system 10, the overall cycling 94 may last for a total of twelve hours according to recommendations. Otherwise, the cycling 94 may continue for all waking hours or all hours that the system 10 is being worn during a day. In one currently contemplated embodiment, an automatic timer may be engaged once the system 10 is activated 90, resulting in cycling 94 for twelve hours, and then automatically shutting down the system 10.

In a second option, the system 10 may be activated 90 to cycle 94 continuously for two hours, with no waiting 98 or delaying 98 between the pulsing 96. Thus, cycling 94 in such a condition results in pulsing 96 one hundred percent of the time for the entire time that the system is activated 90.

Recommended pulsing 96 as a continuous operation is two hours. This corresponds well with physical activity, which typically does not last much longer than two hours, due to the strain of the exercise. Thus, athletic events, climbing, running, and the like for which a continuous pulsing 96 fills the entire cycling 94, will typically not last longer than two hours. Thus, a recommended time of two hours is provided. Likewise, an automatic shut off in two hours may occur.

Various examples have been developed for use of the system 10. Accordingly, certain experimental uses have provided results. In a system 10 in accordance with the invention, the operation of the system 10 is directed specifically and exclusively not at bones or muscles, but at blood vessels.

The function of the system 10 is not to act directly on tissue cells. Rather, the function of the system 10 is to free up the individual blood cells 70 from their aggregations 72. The process of diffusion under Fick's law, discussed hereinabove, demonstrates that the delivery of nutrients and oxygen to cells in the body operates by passage from the digestive tract and lungs into the bloodstream and from the bloodstreams to individual cells.

The necessary vitamins, minerals, and other nutrients are required to operate the cells of the body. The cellular activity in the body is typically a combination of chemical reactions that amount to "combustion" or "consumption" of nutrients in order to release energy, measured in calories or kilocalories. To that end, vitamins are considered, generally, to be the chemicals as antioxidants to escort waste products safely away from the operating tissue cells into the bloodstream. Waste products result from cellular reactions, a "combustion" process, by which cells release and consume energy.

Similarly, minerals are typically metal-based and operate as catalysts. The energy release processes or chemical reactions within tissue cells rely on minerals and the metals in minerals to operate as catalysts in the chemical reactions. Catalysts chemically reduce the threshold energy required to cause reactions to occur.

Thus, minerals participate in the energy generation processes or breaking down of the nutrients that a body receives as food, providing catalysis for the chemical-breakdown reactions. The vitamins provide antioxidants to prevent cell damage that might otherwise be done by waste products reacting undesirably with any other chemical species or cell constituents on the path of those waste products in exiting the body. Thus, vitamins provide a very important antioxidant and removal function.

The vascular system of a body thus carries nutrients through arteries, and returns waste products to the veins. The lungs bring oxygen to the bloodstream in order to participate in the energy release of energy-releasing reactions. The lungs also extract from the bloodstream carbon dioxide as a waste product and discharge it into the atmosphere. Similarly, the digestive tract extracts nutrients from food, putting them into the bloodstream, and the kidneys extract waste products from the bloodstream.

Thus, in a system 10 and method 80 in accordance with the invention, an objective and functionality of the system 10 and process 80 need not directly affect cellular activity in the body. Rather, by enabling the blood cells 70 to separate from their aggregations 72 and distribute more evenly within the plasma 74, greater surface area is available to participate in chemical reactions and transport processes such as diffusions of chemical species to and through walls of cells 70.

In actual electro micrographs (images from a scanning electron microscope), the actual individual cell 70 and aggregation 72 may be easily discerned. In accordance with the description of FIGS. 11 and 12 hereinabove, aggregations 72 observed in actual blood samples before and after application of the system 10 and method 80 reveal the substantial effect, separating individual cells 70 from one another. Aggregations 72 have been counted in the chains 72 or stacks 72 greater than a dozen.

According to calculations typical of the experiments conducted, the flat sides or the approximately circular side faces of a cell 70, each constitute about 28.5 percent of the surface area available in a cell 70. Meanwhile, the rim that remains exposed when multiple cells 70 are aggregated 72 constitutes about 43 percent of the total available surface area of the cell 70. Thus, with an aggregation 72 of about eight cells 70, the 100 percent surface area available for a cell 70 to exchange chemical species with the surrounding plasma 74 is reduced by about 50 percent. Again, if fewer cells 70 aggregate 72, then there is less reduction in the availability of surface area for transport. Nevertheless, aggregations 72 far greater than a dozen cells 70 have been literally counted in the actual electro-micrographs from a scanning electron microscope (SEM) photographing (imaging) blood samples of actual individuals.

In experiments, the system 10 in accordance with the invention effectively eliminated aggregations 72. A blood vessel is a three-dimensional object, and the lumen (passage) is a three-dimensional space. Accordingly, cells 70 will still make contact, and pass one another. However, the tendency to aggregate 72 appears to be effectively remediated virtually completely by a system 10 in accordance with the invention.

Tests have been conducted on over fifty individuals. The samples have been reviewed microscopically before and after application of micro-coils 40 of the system 10. In each case, the regimen applying the electromagnetics effects to blood vessels, as described, results in separation of red blood cells 70, erythrocytes 70, from one another within the plasma 74 effectively reversing the effects of aggregations 72.

It has been found in a system 10 in accordance with the invention that oxygen saturation levels or the amount of oxygen that can be stored or that is actually stored in the bloodstream can be tested, and has proven to be raised substantially by an application on the process 80 in a system 10 in accordance with the invention. Autoimmune diseases all appear to have the difficulty of erythrocyte aggregation. Hundreds of studies have demonstrated the presence of aggregations 72 due to the presence of autoimmune diseases, inflammation, and the like.

Capillaries are comparatively small, compared to blood vessels that carry and distribute blood to capillaries. For example, the aorta and the vascular structures around the heart are many thousands of times larger than individual blood cells. Blood vessels (arteries and veins) exist in an assortment of sizes between capillaries that at the smallest may pass individual blood cells 70 within plasma 74 and not be able to fit multiple cells 70 therein.

Thus, thrombosis (clogging) in capillaries, arteries, and veins, may occur more easily in the presence of aggregations 72. Typically, healthy blood will eventually separate individual cells 70 from aggregations 72 as blood vessels divide. That is, mechanical shear of flow will separate cells 70 from one another. However, in unhealthy persons or unhealthy bloodstreams, aggregations 72 may not break up due to several factors. Various health factors with respect to individual cells 70 themselves may exist to interfere with division of aggregations 72. Also, secondary effects, such as inflammation and dehydration may reduce the plasma 74 volume or its viscosity (resistance to flow), thus limiting the natural ability of flow in plasma 74 to separate individual cells 70 to pass through capillaries. Thus, a system 10 in accordance with the invention greatly enhances the capillary traffic or flow in transport processes.

Cells 70 are individuated (separated to travel alone), thus greatly enhancing the ability of the bloodstream to divide in arteries to continue to subdivide through smaller arteries, and to ultimately divide among capillaries. This results in greater proportion of the surface area on the cells 70 available to deliver nutrients and take up waste products. Meanwhile, the ability to flow is enhanced, thus improving circulation. Circulation itself, simply by occurring, provides more cells 70 passing any particular location in a wall of a capillary, and thereby enhancing the overall macroscopic transport by increased flow. Meanwhile, the individual exposure of the full cell wall on the cell 70 is also greatly enhanced by separating aggregations 72 into individual cells 70.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for remediation of erythrocyte aggregation in vivo, the method
comprising:
    providing micro-coils, as electromagnets, on metallic cores as flux guides;
    selecting a blood vessel region containing a targeted blood vessel in a live subject;
    positioning the cored micro-coils directly over the blood vessel region;
    pulsing the micro-coils to induce a pulsed electromagnetic field (PEMF) into the targeted blood vessel; and
    cycling the electromagnetic field between an on condition and an off condition until dis-aggregation of the erythrocytes has occurred in the targeted blood vessel.

2. The method of claim 1, comprising selecting a bodily member containing the targeted blood vessel passing near an outer surface of skin thereon.

3. The method of claim 2, further comprising:
    setting a regimen for the cycling to include the PEMF during the on portion of time, and ceasing the pulsed electromagnetic fields during an off condition.

4. The method of claim 1, wherein the cycling comprises;
    establishing a regimen having a cycle including an on time constituting a period of time in which the PEMF is applied, and a wait time during which no PEMF is applied; and
    maintaining the dis-aggregation throughout a bloodstream of the live subject by repeating the cycle continually, based on the regimen.

5. The method of claim 4, further comprising deactivating the micro-coils and removing the micro-coils from the skin of a user.

6. The method of claim 5, further comprising:
    providing a wearable band containing the micro-coils; and
    positioning the micro-coils by wrapping and securing the band about a bodily member of the live subject.

7. The method of claim 6, comprising:
    providing a battery operably connected to the micro-coils to provide electrical power thereto; and
    recharging the battery without electrical contact with the battery.

8. The method of claim 1, further comprising:
    providing a housing and a strap;
    positioning the micro-coils in the housing, operably connected to secure a member of a body of the live subject with the strap; and
    applying the micro-coils to the member by wrapping the strap around the member and securing the strap against removal therefrom.

9. The method of claim 8, comprising providing the housing and strap to move with the member throughout a daily routine without necessitating a removal.

10. The method of claim 1, comprising:
providing a band containing a strap operably secured to a housing to receive the micro-coils;
securing the band to a selected member of the live subject; and
operating the micro-coils until the dis-aggregation has occurred throughout an entire circulatory system of the subject.

11. An apparatus for use on a live subject, the apparatus comprising:
a micro-coil constituted by wire wrapped around a metallic core acting as a flux guide for magnetic flux generated by electricity through the wire;
a battery operably connected to selectively pulse electricity from the battery through the micro-coil;
a band sized to receive the micro-coil and battery therein; and
a strap formed to secure the micro-coil by wrapping around a bodily member of the live subject to pass a PEMF through a targeted blood vessel conducting blood thereby remediating the blood of erythrocyte aggregation.

12. The apparatus of claim 11, comprising a cassette containing the battery and the micro-coil.

13. The apparatus of claim 12, comprising a housing holding the cassette in the band.

14. The apparatus of claim 13, wherein the band and housing are homogenously molded with the strap.

15. The apparatus of claim 14, further comprising a securement mechanism sized, shaped, and operably configured to wrap securely around the bodily member to fasten thereto and move therewith throughout daily activities.

16. The apparatus of claim 15, comprising a cap removable from the cassette to selectively seal the cassette against a surrounding environment, and to open the cassette to replace the battery therein.

17. The apparatus of claim 16, comprising a first transformer half selectively positionable proximate the cassette and effective to recharge the battery.

18. The apparatus of claim 17, wherein the micro-coil is configured as a mating half transformer effective to transform electromagnetic flux from the first transformer half through the micro-coil into an electrical current to recharge the battery.

19. A method of remediating erythrocyte aggregation in a live subject comprising:
positioning a micro-coil having a wire coiled to generate a magnetic flux in a metallic core thereof to direct a PEMF into a selected blood vessel of the subject;
energizing the micro-coil by a battery:
rendering the micro-coil portable during generation of the PEMF through the blood vessel; and
remediating erythrocyte aggregation in the subject by applying and controlling a frequency and current discharged from the battery to the micro-coil to control a duty cycle of the micro-coil passing electromagnetic flux in accordance with a pre-determined regimen.

20. The method of claim 19, comprising enclosing the micro-coil and battery in a wearable, mobile article configured to wear on a wrist of the live subject analogously to a watch.

* * * * *